United States Patent [19]

Zeimer et al.

[11] Patent Number: 5,546,941
[45] Date of Patent: Aug. 20, 1996

[54] PATIENT OPERATED TONOMETERS

[75] Inventors: Ran C. Zeimer, Reisterstown, Md.;
George J. Jost, Lake In The Hills, Ill.;
Robert C. Bainbridge, Sandwich, Ill.;
Richard Schwarzbach, Naperville, Ill.;
Charles Ware, Warrenville, Ill.;
Kathleen D. Zebrowski, Hinsdale, Ill.

[73] Assignee: CDS Technologies, L.L.C., West Chicago, Ill.

[21] Appl. No.: 330,981

[22] Filed: Oct. 28, 1994

[51] Int. Cl.$^6$ ......................................................... A61B 3/16
[52] U.S. Cl. ............................ 128/652; 128/645; 128/651
[58] Field of Search ................................... 128/645, 651, 128/652; 73/82; 351/212, 213

[56] References Cited

U.S. PATENT DOCUMENTS

| | | | |
|---|---|---|---|
| 3,756,073 | 9/1973 | Lavallee . | |
| 3,832,890 | 9/1974 | Grolman . | |
| 3,889,518 | 6/1975 | Denouter . | |
| 4,951,671 | 8/1990 | Coan | 128/652 |
| 5,070,875 | 12/1991 | Falck et al. | 128/645 |
| 5,100,227 | 3/1992 | Winocur | 351/212 |
| 5,190,042 | 3/1993 | Hock | 128/652 |
| 5,203,331 | 4/1993 | Draeger | 128/652 |

OTHER PUBLICATIONS

IEEE Transactions on Biomedical Engineering–Instrument for Self–Measurement.
Archives of Ophthalmology, Evaluation of Self Tonometer for Home Use.
Archives of Ophthalmology, Application of a Self–Tonometer to Home Tonometry.
Archives of Ophthalmology, Self Tonometry to Manage Patients with Glaucoma.
Ophthalmology, Presence and Rapid Decline of Early Morning Intraocular Pressure.

*Primary Examiner*—Angela D. Sykes
*Assistant Examiner*—Bryan Yarnell
*Attorney, Agent, or Firm*—Patnaude, Videbeck & Marsh

[57] ABSTRACT

An improved tenometer provides for a bellows and a stepper motor to pressurize the interior of a probe in the barrel into which the probe is fitted for moving the probe outward towards a patient's eye. The device also includes a laser for improved centering of the patient's eye over the eye piece, and a safety detection device for terminating operation of the tenometer if the probe fails to move along the barrel after a given amount of pressure is applied to the interior of the barrel and the probe. A rotatable occluder near the head rest for blocking the eye not being tested and a computer in the instrument records the eye being tested and the test results.

19 Claims, 5 Drawing Sheets

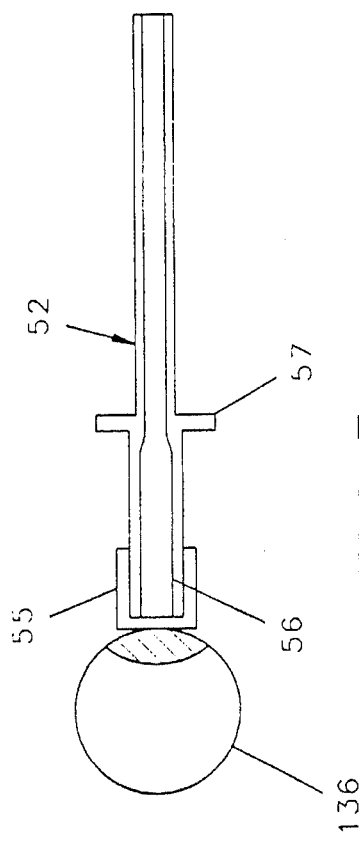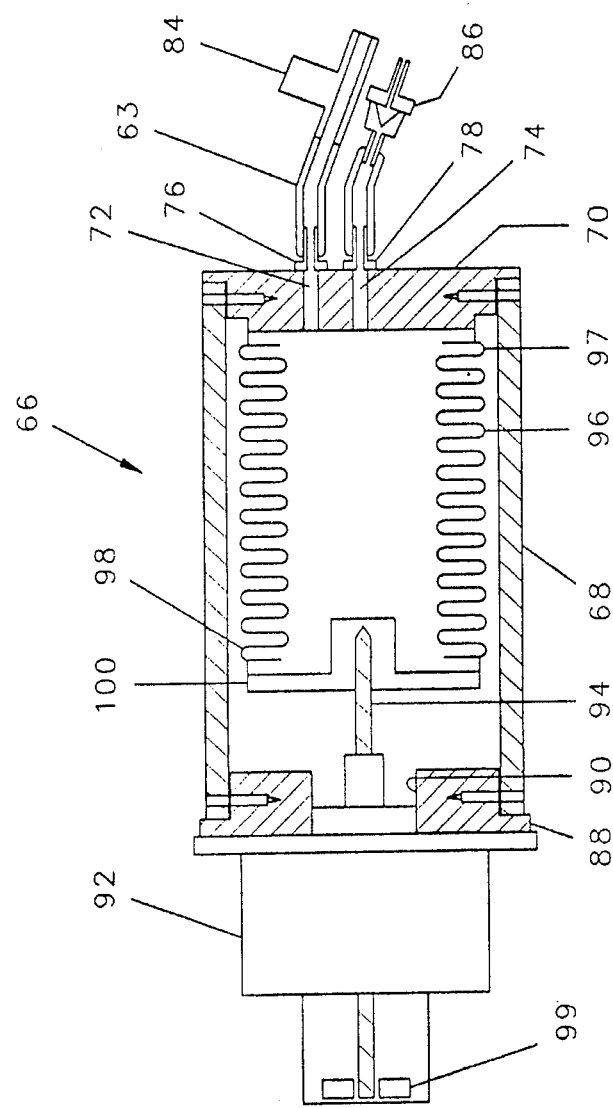

PATIENT OPERATED TONOMETERS

The present invention relates to tonometers, and in particular to tonometers which can be used by a patient to test eye pressure at home.

BACKGROUND OF THE INVENTION

Glaucoma is a disease of the eye which is not curable, but treatable, especially when detected in an early stage. Glaucoma results in elevated intraocular pressure, or IOP which causes damage to the optic nerve and loss of vision.

The usual test for glaucoma is to measure the IOP of a patient's eye, however it has been found that the IOP is not a constant. Even in normal eyes varies throughout the course of the day. For normal eyes, the diurnal variation may range between 3 and 12 mmHg. For patients suffering from glaucoma, the diurnal variation is substantially greater, typically ranging from 11 to 19 mmHg. but may, on occasion, reach 50 mmHg. As a result, a ophthalmologist can not rely upon results from a single tonometer test given to a patient in the office to determine whether the IOP of his or her eye is elevated. When a patient is suspected of having glaucoma, it is therefore desirable to test the IOP of a patient's eyes several times during the course of a day, and over a period of several days to determine an average IOP, and the maximum IOP for the patient. To undertake such tests, it is desirable to have a tonometer which can be operated at home by the patient without the assistance of a technician.

Efforts have been made to develop a patient operated tonometer, however certain problems have been encountered in the development of the device.

One problem arises from the delicacy of the human eye. To read the IOP of a patient's eye, a probe must first be positioned against the patient's eye, and thereafter the pressure of the probe against the eye must be gradually increased until the cornea of the eye is caused to applanate. The device must read the pressure at which the cornea of the eye is caused to applanate. To measure the small pressures within the eye, pressurized air is used to telescope a probe against the eye of the patient and the pressure of the air measured to determine IOP. Even though it is customary to anesthetize a patient's eye, patients have difficulty tolerating the contact of a probe to the eye, and the patient's sensitivity has resulted in inaccurate readings of such tonometers.

Previously developed patient operated tonometers have a probe slidable within a fixed barrel, and pressurized air is applied within the barrel to move the probe against a patient's eye. Unfortunately, existing devices do not monitor the movement of the probe within the barrel, and the probes of existing tonometers can be accelerated down the barrel by the increasing air pressure applied in the barrel, such that the probe can cause injury to the patient's eye. This danger is compounded if the probe should "stick" as the pressure in the barrel is increased. When the air pressure is sufficiently high to free the probe, it may be rapidly propelled into the patient's eye causing injury.

Another difficulty encountered with patient operated tonometers is that the accurate readings of IOP requires that the measurement be taken from the center of the cornea of the eye. Existing patient operated tonometers provide for a conventional light source aligned with the center of the axis of the probe, and the patient is instructed to focus his or her eye on the light source. Such methods have not resulted in the accurate alignment of the eye because such light sources direct a wide pattern of light against the retina of the patient's eye, and the patient has difficulty focusing on the center of the source, which is required if the cornea of the eye is to be centered over the probe.

In order to provide a tonometer which can be used in a patient's home, without the existence of a technician and which will provide accurate readings of IOP, the foregoing problems must be overcome.

SUMMARY OF THE INVENTION

In order to cause a minimum discomfort to a patient it is desirable that the probe of a tonometer be moved against the cornea of the eye with a minimum of force, and that contact of the probe against the eye occur shortly after the test has commenced. After the probe has contacted the eye, it is desirable that the pressure of the probe be raised rapidly, so as to complete the test before the patient withdraws his or her head from the probe. It has been found that it is desirable to vary the pressurization of air behind the probe during the course of the test so as to achieve the results desired. At the commencement of the test, the pressure of air behind the probe must be elevated at a first rate to overcome the static inertia of the probe. Once the probe is in motion towards the patient's eye, the rate of application of pressure behind the probe can be reduced to a second lower rate or fixed, such that the probe is not excellerated. Finally, after the probe has contacted the eye, the air pressure behind the probe must be rapidly elevated such that applanation occurs prior to the patient's withdrawing his or her head from the probe.

The present invention is embodied in a tonometer which includes a retaining barrel having a first open end, a closed second end, and a polished cylindrical shaft into which is fitted an elongate tubular probe having a flexible transparent membrane across the distal end thereof. To minimize the resistance of the probe as the probe moves within the barrel, the probe is precision machined and the surface thereof is polished.

To pressurize the barrel, it is preferable to use a bellows rather than a piston as has been used in previous devices, because the pressure generated by a bellows can be accurately controlled. Also, it has been found that a bellows has a longer useful life without leakage than does a piston operated device.

To drive the bellows, it is desirable to use a stepper motor because the speed of a stepper motor can be accurately controlled by a computer, which is not the case for other electric motors.

To prevent injury to the eye caused by the probe first "sticking" in the barrel, and then snapping towards the patient's eye after it has been freed, a sensor is provided within the barrel to detect when the probe has commenced moving. If the probe does not commence movement down the barrel within a given time after the air pressure in the barrel is elevated, a computer which is connected to the sensor and the motor, will turn off the motor and abort the test, thereby preventing injury to the patient's eye.

In accordance with the present invention, a laser beam is directed through a 1% transmittance filter, and through a 50% transmittance beam splitter, and into the probe. This beam splitter is angled, preferably at a 45 degree angle relative to the axis of the probe such that a portion of the light from the laser is directed down the length of the probe to the membrane at the distal end thereof. At applanation, a portion of the light is reflected by the membrane, down the barrel of the probe and off the angled beam splitter into a detector. A pressure detector records the pressure of the air in the sleeve and the probe at the instant of applanation.

To center a patient's eye with respect to the probe, a plurality of light emitting diodes (LED's) are spaced around the inner surface of the barrel. When the laser beam and LED's are viewed by the patient through the eye piece, the patient will see a pattern of lights surrounding a red spot from the laser. The patient's eye is properly centered before the eye piece when The patient sees the spot from the laser centered within the pattern of lights.

To assist in the positioning of the patient's eye over the probe, an eye support is provided. The eye support has first and second padded portions, positioned above and below the eye respectively, and behind the eye support is a rotatable occluder having an arm and an eye cup at the distal end thereof for blocking vision through the eye which is not being tested. A sensor detects which eye is covered by the occluder and the computer records separately, the test results for each eye.

A patient using the tonometer embodying the present invention first positions the eye to me tested in front of the probe with his or her head against the padded portions of the support, and the cup blocking the view to the other eye. When looking into the end of the probe, the patient will see a deep red spot of light from the laser centered within the LED's without his or her attention being distracted by the eye not being tested. After a number of tests typically four, are conducted on one eye of the patient, the occluder is pivoted around the axis of the probe through a 180 degrees such that the arm is extending from the opposite direction, and can be used to block the eye previously tested while the second eye is tested.

GENERAL DESCRIPTION OF THE DRAWINGS

A better understanding of the present invention will be had after reading the following detailed description taken in conjunction with the accompanying drawings wherein;

FIG. 3 is an enlarged cross-section of the probe;

FIG. 4 is an enlarged cross-sectional view of the bellows and stepper motor in the tonometer shown in FIG. 1;

DETAILED DESCRIPTION OF A PREFERRED EMBODIMENT

Figure 1:
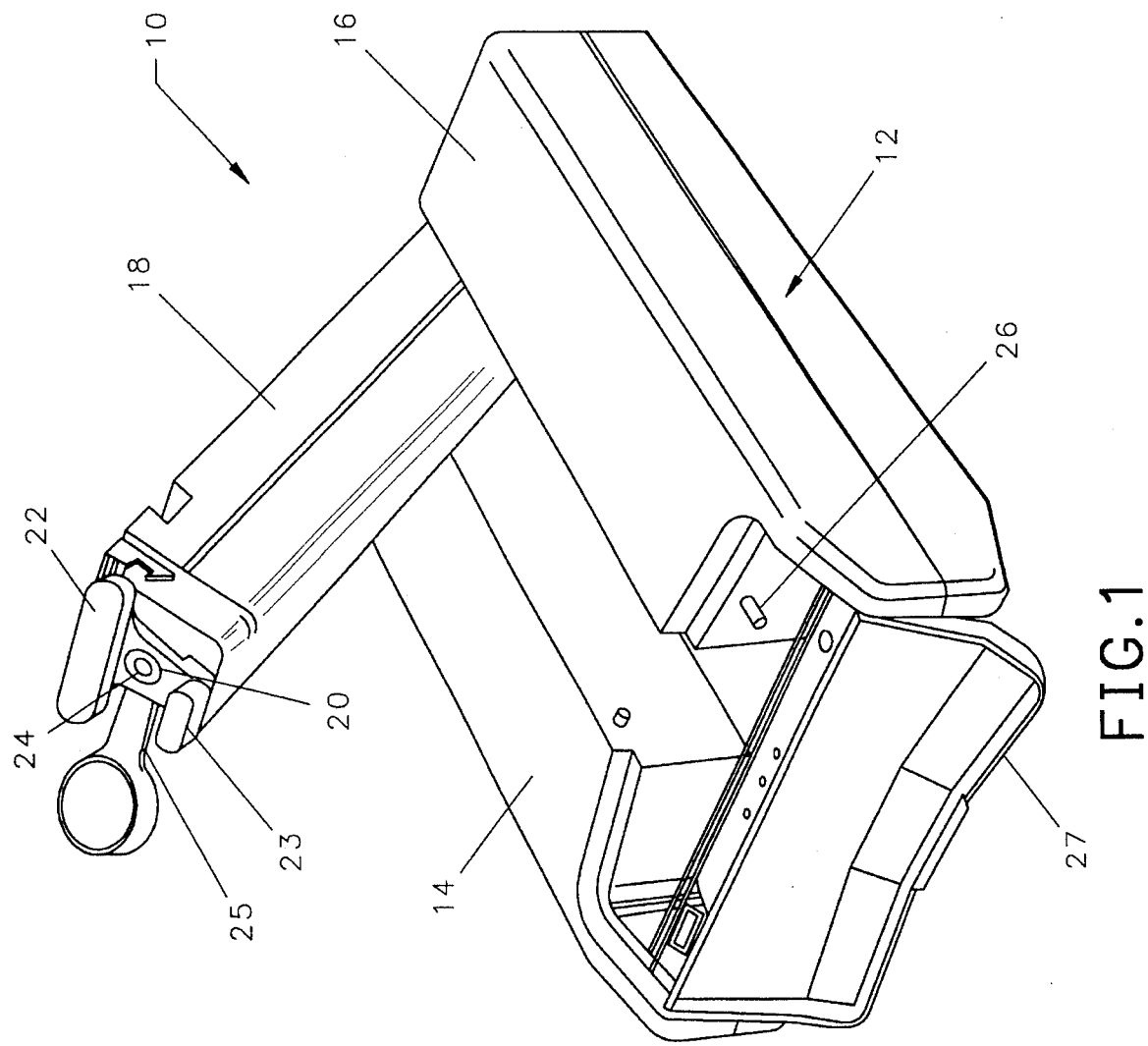
FIG. 1 is a perspective view of a tonometer in accordance with the present invention.

Referring to FIG. 1, a tonometer 10 includes a housing 12 with a first and second parallel enclosures 14,16 between which is fitted a pivotable arm 18. At the distal end of arm 18 is an eye piece 20 having upper and lower face cushions 22,23 and a central opening 24 through which a probe, not shown, can extend. Behind the eye piece 20 is a rotatable occluder 25. As depicted in FIG. 1, the moveable arm 18 is in the elevated position such that when the tonometer 10 is on a level surface, a patient can position his or her face against the cushions 22,23, with the pupil of his or her eye positioned over the central opening 24. The moveable arm 18 may also be rotated to a lower position where it is fitted between the first and second enclosures 14,16 for transporting the device. A button 26 is easily reachable by a patient who can depress the button 26 to start a test. Also, a protective cover 27 is provided which can cover the eye piece 20 and central opening 24 of the arm 18 such that the device 10 can be transported without damage to the parts thereof.

Figure 2:
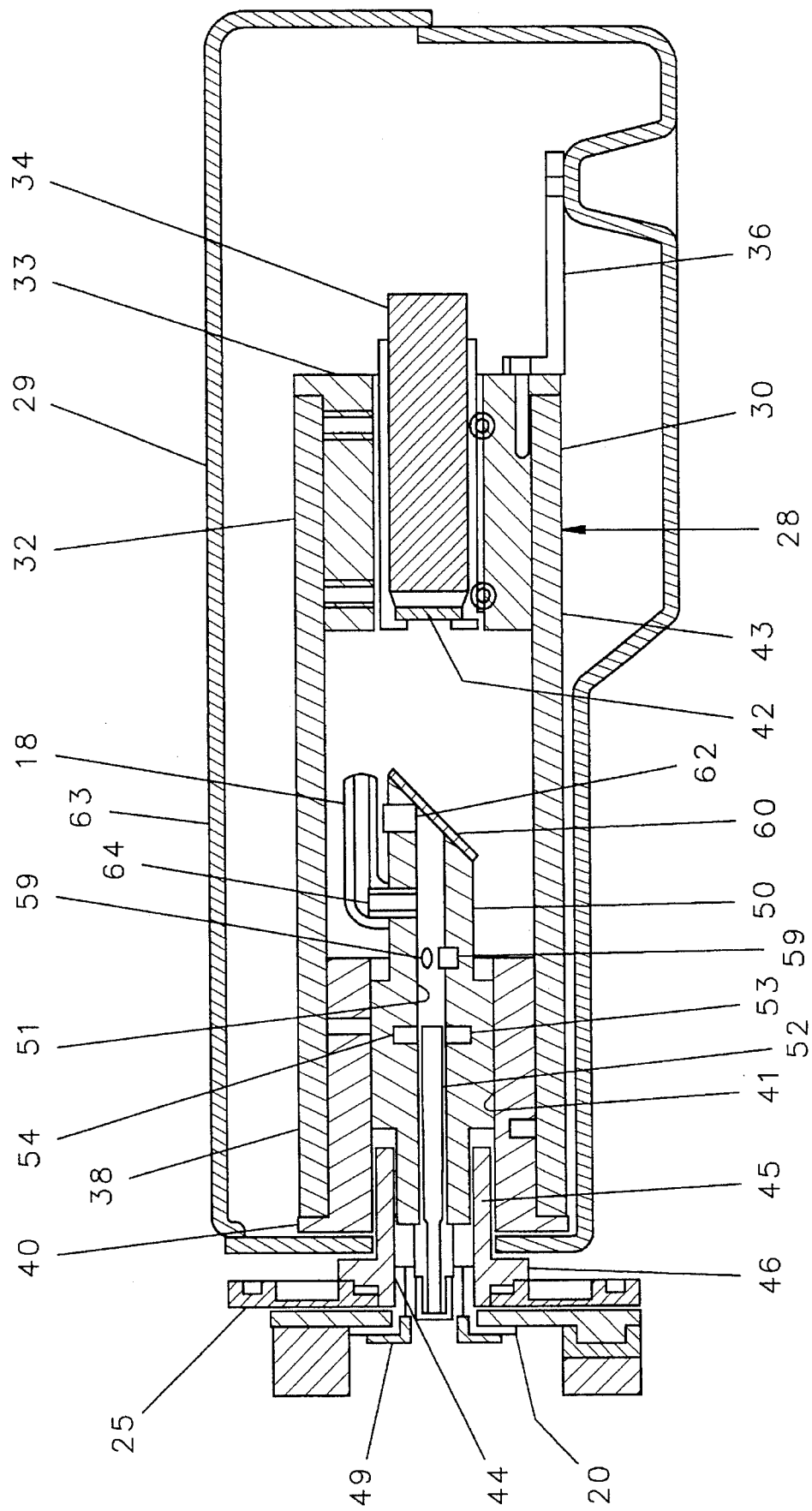
FIG. 2 is an enlarged cross-sectional view of the light module and probe in the tonometer shown in FIG. 1.

Referring to FIG. 2, at the distal end of the arm 18 is a light and probe module 28. Within the housing 29 of the module 28 is an elongate mounting tube 30, into one end 32 of which is fitted a first tubular end cap 33, and within the end cap 33 is a cylindrical laser 34. At the forward end 43 of the first end cap 33 is a 1% transmittance filter oriented perpendicular to the axis of the laser 34. The end cap 33 also has bolted thereto a bracket 36 for securing the first end 33 of the mounting tube 30 to the housing 29.

At the second end 38 of the mounting tube 30 is a second tubular end cap 40, having an axial central bore 41. The mounting tube 30 is axially aligned with a circular opening 44 in the distal end of the housing 29, and is retained in alignment therewith by a plug 45 having an outer flange 46 which is larger in diameter than the circular opening 44, and a tubular inner end which engages the inner surface of the end cap 40. Pivotally fitted around the outer surface of the forward end of the plug 45 is the rotatable occluder 25, which is retained by the eye piece 48 having a tubular end fitted in the end of the plug 45. Fitted within the eye piece 20 is a tubular probe stop 49 having an inner diameter which will permit the outer end of the probe to pass there through, but will stop an annular flange on the probe, as further described below.

Within the bore 41 of the end cap 40 is a tubular barrel 50, and slidable within the inner opening of the tubular barrel 50 is an elongate hollow probe 52, adapted to slide outward of the forward end 54 thereof. Centrally located on one side of the inner surface of the barrel is a lamp 53 and diametrically opposed to the lamp is an optical switch 54 which are positioned such that the rear end of the probe 52 will interrupt the light beam to the switch 54 when the probe is fully retracted within the barrel, as shown in FIG. 2.

Referring to FIGS. 2 and 3, the probe 52 has a membrane 55 fitted around its forward end 56 and midway along its length is an outer flange 57. The outer diameter of the flange 57 is greater than the inner diameter of the probe stop 49 so that forward movement of the probe 52 will stop when the flange 57 contacts the inner end of the probe stop 49.

Referring to FIG. 2, across the second end 58 of the barrel 50 is a 50% beam splitter 60 positioned at a 45 degree angle to the axis of the barrel 50. Light emitted from the laser 34 which passes through the filter 42, will be directed to the 50% beam splitter 60. 50% of the light striking the beam splitter 50 will be passed through the length of the probe 52 to the inner surface of the membrane 56. Light reflected by the membrane 56 will be directed back down the barrel 50 and will strike the inner surface of the beam splitter 60, and 50% of that light will be reflected to a light detecting sensor 62, such as a darlington photo transistor, fitted in the side of the barrel 50.

Spaced around the inner surface 51 of the barrel 50 are a plurality of LED's 59 which are recessed into the inner surface 51 so as not to obstruct light from the laser 34 directed down the barrel 50 and the probe 52. In the preferred embodiment, there are three LED's 51 spaced 120 degrees from one another around the inner surface 51 of the barrel 50. When the LED's are viewed by a patient who positions his or her eye to look down the center of the probe and the barrel, the patient will see a pattern of light from the LED's and a red spot from the laser. To center his or her eye before the eye piece the patient moves his or her head until the red spot of the laser is centered within the pattern of lights. The LED's enable a patient to find points of reference which correspond to the walls of the barrel, and therefore, to center the eye. Without the LED's the patient must move his or her head until he or she can approximate the centering of the laser as seen through the eye piece.

A pressure line 63 is connected to a port 64 in the wall of the tubular barrel 50 for pressurizing the air in the bore of the barrel and the inner shaft of the probe 52.

Referring to FIG. 4 fitted within the first enclosure 14 of the housing 12 is a pressure generating module 66. The pressure module 66 includes a tubular housing 68 with a first plug 70 at one end thereof having two transverse bores 72,74 there through into which are inserted tubular fittings, 76,78 respectively, each of which has an end extending outward of the plug 70. Secured over the end of fitting 78 is the second end of pressure line 63, the first end of which is attached to the barrel 50 of the light and probe module 28. Similarly attached around fitting 78 is a second pressure line 82 which is attached to a pressure sensor 84 and a relief valve 86.

At the other end of the housing 68 is a second plug 88 having a cylindrical inner bore 90 and attached to the outer surface of the second plug 88 is a stepper motor 92. The stepper motor advances an axial shaft 94 through the bore 90 of the second plug 88 and into the central opening of the housing 68.

Within the housing 68 is a compressible bellows 96, one end 97 of which is attached to the first plug 70, and the other end 98 of which is attached to a second plug 100 fitted at the distal end of the housing 68. Forward operation of the stepper motor 92, will result in the extension of the shaft 94 into the housing 68 and compression of the bellow 96. At the outer end of the stepper motor 92 is an optical switch 99 which is interrupted when the shaft 94 is fully withdrawn, and the bellows 96 are fully expanded. Compression of the bellows 96 will result in elevated air pressure within the shaft of the barrel 50 and the probe 52 and that pressure will be monitored by the pressure sensor 84.

Figure 5:
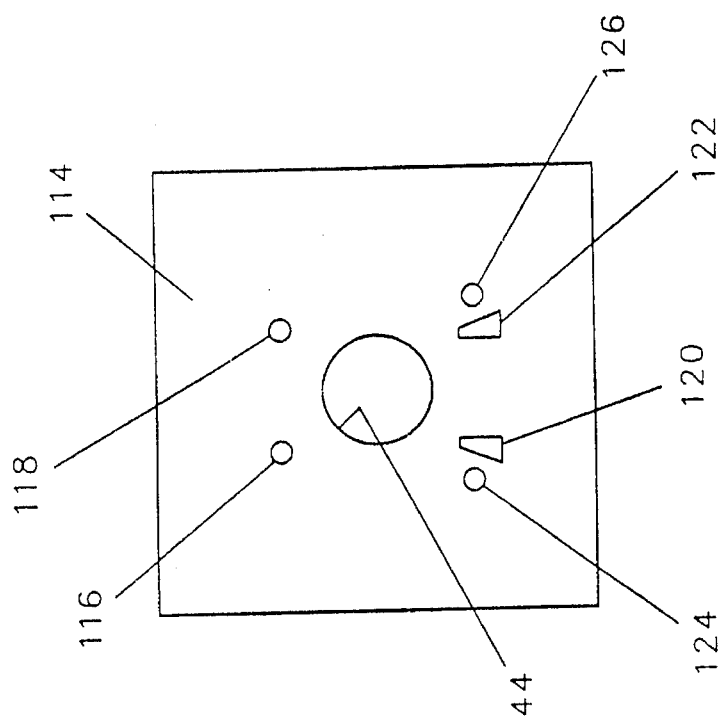
FIG. 5 is a front elevational view of the forward end of the arm with the eye piece and occluder removed.

Referring to FIG. 5, it can be seen that positioned around the opening 44 are a pair of indicator lights 116,118, a pair of stops 120,122 and a pair of switches 124,126. In the preferred embodiment, light 116 is green and light 118 is red. The stops 120,122 are positioned to abut against complimentary stops on the rear surface of the occluder so as to limit rotation of the occluder to 180 degrees.

Figure 6:
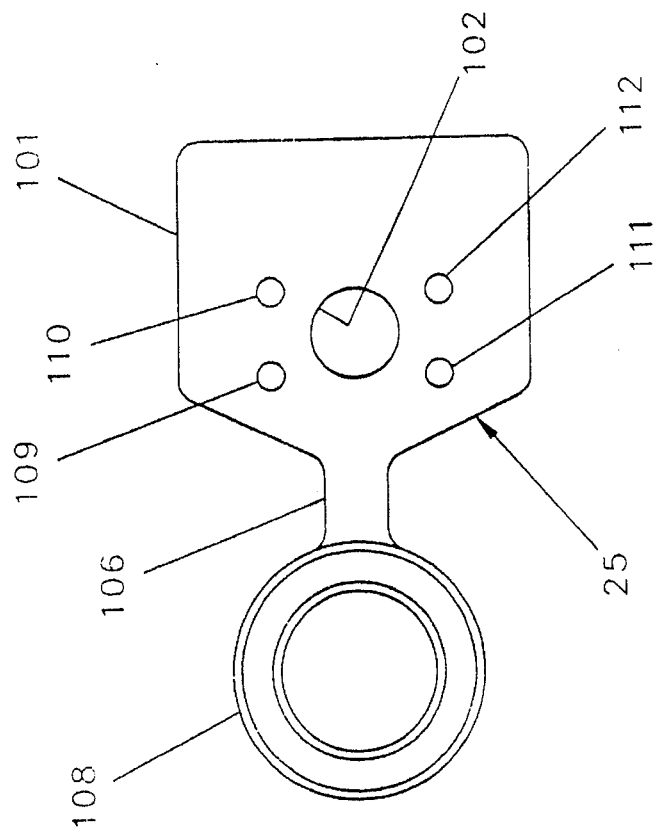
FIG. 6 is a front elevational view of the rotatable occluder for the tonometer shown in FIG. 1.

Referring to FIG. 6, the occluder 25 has a somewhat planer body 101 with a central opening 102 there through, through which the eye piece 48 is fitted to retain the occluder across the forward end of the housing 29. Extending from the body 101 is an arm 106, and at the distal end of the arm 106 is a cup 108 which is sized to fit over the eye of a patient. On the rearward side of the occluder 25, are stops, not shown, which are positioned to encounter the stops 120,122 on the housing 29, such that the occluder 29 can be rotated 180 degrees. The stops are positioned such that the occluder has a first position, in which the cup 108 will cover the patient's left eye, as shown in FIG. 1, or can be rotated 180 degrees to a second position in which the cup 108 will cover the patient's right eye. The body 101 of the occluder further has two pairs of holes, a first pair 109,110 positioned 180 degrees apart from the second pair 111,112, which are located such that the first pair of holes 109,110 will be positioned over indicator lights 116,118 respectively on the front surface of the arm when the occluder 25 is in its first position, and the second pair of holes 111,112 respectively will be positioned over the indicator lights 116,118 when the occluder 25 is in the second position.

Each of the switches 124,126 is positioned near one of the stops 120,122, respectively, and each of the switches 124, 126 is actuated by the corresponding stop on the rear surface of the occluder which is adapted to contact the complimentary stop 120,122 on the arm. Accordingly, when the occluder is in its first position with a stop, not shown, thereof abutting against stop 120 of the arm, switch 124 will be actuated indicating to the computer that the occluder is in the first position. Conversely, when the occluder has rotated 180 degrees to the second position where it will extend across the right eye of the patient, a stop, not shown, thereon will abut against stop 122 of the arm 18, and actuate switch 126 indicating to the computer that the occluder is in the second position.

Figure 7:
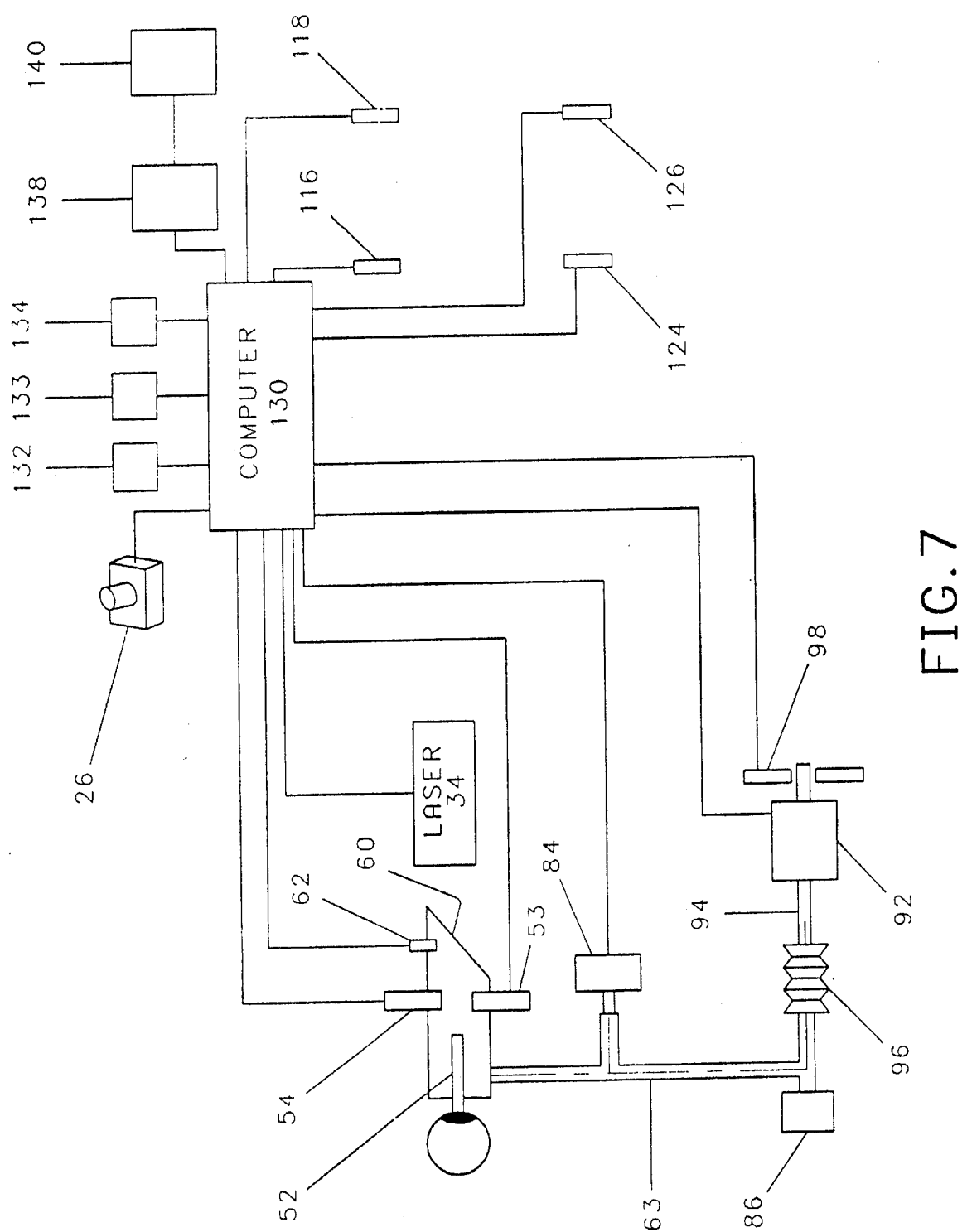
FIG. 7 is a block diagram of the circuit for the tonometer shown in FIG. 1.

Referring to FIG. 7, the device further includes a computer 130, three timer crcuits 132,133,134, a digital memory 138 and an output terminal 140 through which the test results stored in the computer can be withdrawn.

When a patient desires to use the tonometer to test eye pressure, he or she will position the tonometer on a flat surface and move the arm to the upward position shown in FIG. 1. At the commencement of the test, the probe 52 will be withdrawn within the barrel 50 and the rearward end will interrupt the light from lamp 52 to the optical switch 54. Also, the stepper motor 92 will have been reversed such that the shaft 94 will be fully withdrawn thereby inflating the bellows 96 and the distal end thereof will interrupt the optical switch 99. Also, the occluder 25 will be rotated to the first position shown in FIG. 1 with the stop on the occluder, not shown, positioned against stop 120 on the arm and the switch 124 actuated. The indicator lights 116,118 will therefore be visible through holes 109,110 of the occluder.

The interrupted optical switches 54,99 and the actuated switch 124 will indicate to the computer that the probe, bellows and occluder are all positioned to commence the test and the computer 130 will carry out a test sequence when the button 26 is actuated by the patient.

When the button 26 is first actuated by a patient, the computer 130 will turn on the LED's 59 and the laser 34 and direct a beam of light down the barrel 50, and the probe 52. A patient will then position his or her right eye before the eye piece 20 and the left eye against the cup 108 of the occluder 25. When the red dot from the laser appears centered in the pattern of lights, the patient will then depress the button 26 again and the computer 130 will commence the test.

The computer 130 will first direct a first sequence of pulses to the stepper motor 92 to operate the stepper motor at a first rate, and the first sequence shall continue for an interval of time as determined by the first timer circuit 132. With the stepper motor moving at the first rate, the shaft 94 will compress the bellows 96 and pressurize the line 62 and the air within the barrel 50 and probe 52. The first timing circuit 132 should allow the stepper motor to operate for a sufficient amount of time for the pressure in the barrel to overcome the static inertia of the probe 52 and cause it to begin moving down the barrel 50, removing the obstruction from optical switch 54. In the event that the probe sticks, and does not commence moving within the barrel when pressure is first applied thereto, the increasing air pressure behind the probe may cause it to snap into the eye of the patient. To avoid such an injury, the computer 130 will terminate power to the stepper motor 92 in the event that the optical switch 54 does not detect movement of the probe 52 within an interval of time as determined by the second timer circuit 133.

Once the probe 52 is in movement down the barrel 50, the computer 130 reduces the speed of the stepper motor 92 to a lesser rate, or even stops the motor 92, such that the pressure in the barrel 50 will not accelerate the probe 50 as it moves towards the patient's eye. The stepper motor is operated at the second rate for a period of time determined by the third timer circuit 134, after which the probe is presumed to have made contact with the patient's eye and to be positioned for a test.

Thereafter, the computer 130 directs a sequence of pulses to the stepper motor 92 to operate it at a third, faster rate, to thereby rapidly compress the bellows 96 and rapidly raise the pressure in the barrel 50.

Referring to FIG. 3, it can be seen that when the probe 52 is positioned with the membrane 55 against the eye 136 of a patient, the membrane 55 of the probe will be indented inward. Light from the laser which passes down the length of the probe 52 will strike the membrane 55 and be deflected outward along the walls of the probe. The stepper motor and bellows 96 will gradually increase the pressure within the probe until it equals the pressure within the eye 136 of the patient, at which point the membrane 55 will become substantially planar and light from the laser 34 will be reflected by the membrane 55 back down the length of the probe 52, off the inner surface of the beam splitter 60 and into the detector 62. When the computer 130 detects a peak in the light being received by the light detecting sensor 62, the computer will record the pressure from the pressure sensor 84.

After the computer 130 has made an applanation reading, the computer 130 will reverse the direction of the stepper motor 92, to withdraw the shaft 94 and inflate the bellows 96. Inflation of the bellows 96 will cause the probe 52 to be drawn down the barrel 50 until the inner end again interrupts the optical switch 54. The relief valve 86 will prevent an excessive vacuum developing within the pressure line 63 and the barrel 50 as the bellows 96 are inflated to the their maximum capacity. When the bellows are fully expanded, the distal end of the shaft 94 will interrupt the optical switch 93, the computer will terminate power to the stepper motor 92, and the tonometer 10 is ready to undertake another test.

When the computer 130 determines that the device is prepared to initiate a test, the green light 116 is illuminated, and conversely when the device is not properly oriented for a test, the red light 118 is illuminated. Each test should consist of four readings of the right eye, followed by four readings of a left eye, and the results of all of the readings are retained within a memory chip 138, for withdrawal from the device 10 machine by the technician through a terminal 140.

To operate the tonometer, a patient first moves the occluder 25 to the first position where the cup 108 will extend to the left for blocking of the patient's left eye, thereby actuating switch 124. The patient then depresses the start button 26. If the input from optical switches 54 and 99 indicate that the probe and bellows are prepared for a test, the computer will illuminate the green light 116 which the patient will see through hole 109 of the occluder. The patient will then position his or her right eye against the eye piece 20 and left eye against the cup 108. When the patient has the beam of the laser 34 centered in his or her eye, the patient will again depress button 26 and the test will commence. The computer will require that four successive tests be conducted for the right eye, thereafter will not permit further tests until the occluder 25 is rotated 180 degrees so as to cover the patient's left eye and actuate switch 126. The computer 130 will then conduct a second series of four tests for the patient's left eye.

In the event a patient moves his or her eye after a test has been commenced, the light detecting sensors 62 may not detect a peak indicative of a applanation. In such an event, the computer will continue to direct power to the stepper motor 92 at the third rate until the pressure sensor 84 determines that the pressure within the probe has reached a maximum level, typically about 50 mmHg, after which the computer will abort the test.

It has therefore been described a tonometer which can be used by a patient in his or her home to undertake a number of tests during the course of a day after which a technician can obtain the results of the test, and an accurate average pressure of the patient's eyes. The present invention can also be used by the patient, without the presence of a technician, without causing injury to the patient's eye.

While the present invention has been described in connection with one embodiment, it will be understood by those skilled in the art that many changes and modifications may be made without departing from the true spirit and scope of the invention. Therefore it is intended by the appended claims to cover all such changes and modifications that come within the true spirit and scope of the invention.

We claim:

1. In a tonometer comprising a barrel having an open forward end, an elongate probe slidable in said open forward end of said barrel, contact means at a forward end of said probe for contacting an eye of a patient, and means for detecting applanation of an eye of a patient, the improvement comprising means for pressurizing said barrel for moving said probe down said barrel, a stepper motor for driving said means for pressurizing said barrel, shaft means connected to said stepper motor for driving said means for pressurizing said barrel, said shaft means having a first position for commencing pressurizing said barrel, and detection means for detecting that said shaft means is in said first position prior to a test.

2. The improvement of claim 1 wherein said means for pressurizing said barrel is a bellows.

3. In a tonometer comprising a barrel having an open forward end, an elongate probe slidable in said open forward end of said barrel, contact means at a forward end of said probe for contacting an eye of a patient, and means for detecting applanation of an eye of a patient, the improvement comprising means for pressurizing said barrel for moving said probe down said barrel, said means for pressurizing having an inflated condition, and a deflated condition, detection means for detecting that said means for pressurizing is in said inflated condition prior to a test.

4. The improvement of claim 3 and wherein said means for pressurizing said barrel is a bellows.

5. The improvement of claim 3 wherein said means for pressurizing comprises a stepper motor.

6. In a tonometer comprising a barrel having an inner surface, and means for detecting applanation of an eye of a patient, the improvement comprising:

laser means for directing a beam of light longitudinally through said barrel, said laser means for centering an eye of a patient before said barrel, and a plurality of light elements spaced around said inner surface.

7. The improvement of claim 6 and further comprising:

occluder means for covering a left eye of a patient when the right eye is before said barrel and for covering a right eye of a patient when the left eye is before said barrel, and means for detecting whether said occluder means is oriented to cover a left eye or a right eye.

8. In a tonometer comprising a barrel having a shaft therein and an open forward end, an elongate probe slideable in said open forward end of said barrel, contact means at a forward end of said probe for contacting an eye of a patient, and means for detecting applanation of an eye of a patient, the improvement comprising means for moving said probe down said barrel, detecting means for detecting movement of said probe down said barrel, and means for terminating a test in the event said detecting means does not detect movement of said probe in response to said means for moving said probe.

9. The improvement of claim 8 wherein said means for terminating a test is a computer programmed to terminate a test if said detecting means does not detect movement of said probe after said means for moving said probe has been activated.

10. In a tonometer for detecting applanation of an eye of a patient, the improvement comprising:

occluder means for covering a left eye of a patient when the right eye is before a probe and for covering a right eye of a patient when the left eye is before said probe, and means for detecting whether said occluder means is oriented to cover a left eye or a right eye.

11. The improvement of claim 10 and further comprising indicator means to indicate whether said occluder means is properly oriented for a test.

12. In a tonometer comprising a barrel having a shaft therein and an open forward end, an elongate probe slideable in said open forward end of said barrel, contact means at a forward end of said probe for contacting an eye of a patient, and means for detecting applanation of an eye of a patient, means for pressurizing said barrel for moving said probe down said barrel, motor means for driving said means for pressurizing said barrel, the improvement comprising:

means for controlling said motor means for operation at a first speed to commence movement of said probe, operation at a second speed while said probe is adapted to move against an eye of a patient, and at a third speed to pressurize said probe to applanation pressure.

13. The improvement of claim 12 wherein said means for controlling said motor means is a computer.

14. The improvement of claim 13 wherein, said means for pressurizing has an inflated position, and said improvement further comprises, detection means for detecting that said means for pressurizing is in said inflated position, and said computer is responsive to said detection means.

15. The improvement of claim 13 and further comprising detection means for detecting movement of said probe down said barrel, and said computer responsive to said detection means for terminating a test in the event said detection means does not detect movement of said probe in response to operating said motor at said first speed.

16. In a tonometer for detecting the IOP of an eye of a patient, said tonometer having an eye piece, the improvement comprising, occluder means for covering a left eye of a patient when the right eye is before said eye piece and for covering a right eye of a patient when the left eye is before said eye piece, means for detecting whether said occluder means is oriented to cover a left eye or a right eye, and indicator means for indicating whether said occluder means is properly oriented for a test.

17. In a tonometer comprising a barrel having an inner surface, and means for detecting applanation of an eye of a patient, the improvement comprising a plurality of light elements spaced around said inner surface.

18. In an tonometer having an eye piece before which the eye of a patient is to be positioned and having means for detecting the applanation of the eye of a patient positioned before said eye piece, the improvement comprising:

occluder means for covering a left eye of a patient when the right eye is before said eye piece and for covering a right eye of a patient when the left eye is before said eye piece, and means for detecting whether said occluder means is oriented to cover a left eye or a right eye.

19. A tonometer comprising:

a barrel having an open forward end, an elongate probe slidable in said open forward end of said barrel, contact means at a forward end of said probe for contacting an eye of a patient, means for detecting applanation of an eye of a patient, means for moving said probe down said barrel, detection means for detecting movement of said probe down said barrel, and means for terminating a test in the event said detection means does not detect movement of said probe in response to said means for moving said probe.

* * * * *

UNITED STATES PATENT AND TRADEMARK OFFICE
CERTIFICATE OF CORRECTION

PATENT NO.  : 5,546,941
DATED       : August 20, 1996
INVENTOR(S) : Zeimer, et al It is certified that error appears in the above-identified patent and that said Letters Patent is hereby corrected as shown below:

In column 3, line 21, after "to" delete "me" and substitute --be--.

In column 4, line 38, after "switch 54" delete "which" and substitute --and the lamp and the switch--

In column 8, line 4, after "and" delete "actuate" and substitute --the-- and after "switch 126" insert --actuated--.

In column 9, line 13, after "means" insert --attached to a forward end of said barrel--.

Signed and Sealed this

Twenty-fifth Day of March, 1997

Attest:

BRUCE LEHMAN

Attesting Officer

Commissioner of Patents and Trademarks